US010729637B2

(12) United States Patent
Ghani et al.

(10) Patent No.: US 10,729,637 B2
(45) Date of Patent: Aug. 4, 2020

(54) COMPOSITIONS SUITABLE AS LEAVE-ON HAIR STYLING COMPOSITIONS AND METHODS OF USE

(71) Applicant: L'OREAL, Paris (FR)

(72) Inventors: Sana Ghani, Elizabeth, NJ (US); Aziza Khader Suleiman, Paterson, NJ (US); Vanessa Decarlo, Clark, NJ (US)

(73) Assignee: L'OREAL, Paris (FR)

( * ) Notice: Subject to any disclaimer, the term of this patent is extended or adjusted under 35 U.S.C. 154(b) by 59 days.

(21) Appl. No.: 15/907,780

(22) Filed: Feb. 28, 2018

(65) Prior Publication Data

US 2019/0262251 A1   Aug. 29, 2019

(51) Int. Cl.
| | | |
|---|---|---|
| *A61K 8/73* | (2006.01) | |
| *A61Q 5/06* | (2006.01) | |
| *A61K 8/04* | (2006.01) | |
| *A61K 8/34* | (2006.01) | |
| *A61Q 5/12* | (2006.01) | |
| *A61Q 19/00* | (2006.01) | |

(52) U.S. Cl.
CPC ............ *A61K 8/73* (2013.01); *A61K 8/042* (2013.01); *A61K 8/345* (2013.01); *A61K 8/732* (2013.01); *A61Q 5/06* (2013.01); *A61Q 5/12* (2013.01); *A61Q 19/00* (2013.01); *A61K 2800/30* (2013.01); *A61K 2800/34* (2013.01); *A61K 2800/594* (2013.01)

(58) Field of Classification Search
None
See application file for complete search history.

(56) References Cited

U.S. PATENT DOCUMENTS

| | | |
|---|---|---|
| 6,685,952 B1 | 2/2004 | Ma et al. |
| 9,918,923 B1 | 3/2018 | Naiberk et al. |
| 2001/0022967 A1 | 9/2001 | Brandt et al. |
| 2009/0074697 A1 | 3/2009 | Huynh |
| 2012/0129937 A1* | 5/2012 | Issleib .................... A61K 8/345 514/560 |
| 2014/0302101 A1 | 10/2014 | Carson |

FOREIGN PATENT DOCUMENTS

| | | |
|---|---|---|
| CN | 105007987 A | 10/2015 |
| WO | WO-2017/097438 A1 | 6/2017 |

OTHER PUBLICATIONS

International Search Report and Written Opinion dated Jul. 2, 2019 for corresponding PCT Application No. PCT/US2019/019753.
Database GNPD; Mintel; "Strengthening Facial Gel", 2016 XP055593113.
Database GNPD, Mintel; "Regenerative Eye Cream," 2015 XP055593115.
Database GNPD; Mintel; "Mild Cleansing Emulsion", 2015 XP055593117.
Database GNPD, Mintel; "Bio-Cellular Matrix Facial Serum", 2012 XP055593120.

* cited by examiner

*Primary Examiner* — Nannette Holloman
(74) *Attorney, Agent, or Firm* — Polsinelli PC

(57) ABSTRACT

The present disclosure relates to compositions suitable as leave-in hairstyling compositions comprising (a) a first polysaccharide comprising inulin; (b) a second polysaccharide comprising carrageenan; (c) a third polysaccharide; and (d) a humectant. The compositions as leave-on hair styling do not require synthetic film-forming polymers nor do they require silicones. The leave-on hair styling compositions are particularly useful in methods for imparting durable styling or shaping benefits to hair.

19 Claims, 2 Drawing Sheets

COMPOSITIONS SUITABLE AS LEAVE-ON HAIR STYLING COMPOSITIONS AND METHODS OF USE

FIELD OF THE DISCLOSURE

The present disclosure relates to leave-on hair styling compositions for treating or styling hair. The leave-on hair styling compositions contain a combination of three polysaccharides and a humectant, and are useful in methods for imparting durable styling or shaping benefits to the hair.

BACKGROUND

Consumers desire new multi-functional hair products that can impart good styling benefits to hair, are durable and impart certain cosmetic characteristic to the hair. Such products should be pleasing to the senses, have innovative, interesting and/or pleasing textures, without loss in functional performance. Furthermore, many consumers prefer hair products that provide a light feel, are easy to apply, and add shine and luster to the hair.

Traditional hair products on the cosmetic market appear in various forms. They range anywhere from solutions, foams, gels, creams, waxes, mousses, sprays, serums, to aerosols and can impart a variety of levels of protection to the hair depending on the state of the hair and the components of the product. Generally, products that are designed to impart styling or shaping benefits to hair are in the form of hair styling or hair care/hair treatment products. Some of these products are often sticky or tacky upon application and once dry, may become stiff and/or "crunchy" (i.e. the film is hard and brittle resulting in a crunching feel or sound when the hair is touched), which is undesirable for many consumers.

Current products for imparting styling or shaping benefits to hair often include water soluble film-forming polymers. Depending on the chemical make-up of these polymers, they may be either soluble in water, or they may be water insoluble polymers which are made water soluble via various chemical modifications, such as neutralization. Solutions comprising these polymers tend to be viscous, i.e. as the concentration of the polymer increases, its viscosity builds up rapidly. Translated to styling applications, as the solvent evaporates, the polymer solution becomes thicker on the hair surface, resulting in a sticky or tacky film.

There is thus a need to provide new products which provide consumers with the desired styling benefits, while minimizing the undesired effects.

SUMMARY

One aspect of the invention pertains to composition comprising:
(a) a first polysaccharide comprising inulin;
(b) a second polysaccharide comprising carrageenan;
(c) a third polysaccharide; and
(d) a humectant.

In one or more embodiments, the compositions are suitable as hair styling compositions. In some embodiments, the second polysaccharide does not comprise a levan polysaccharide. In further embodiments, the composition does not comprise a levan polysaccharide. In one or more embodiments, the inulin is present in an amount of from about 0.1 to about 10 wt. %. In some embodiments, the inulin is present in an amount of from about 0.5 to about 2.5 wt %. In one or more embodiments, the carrageenan is present in an amount of from about 0.01 to about 10 wt. % by weight of the total composition. In some embodiments, the carrageenan is present in an amount of from about 0.5 to about 6 wt. % by weight of the total composition. In one or more embodiments, the third polysaccharide is present in an amount of from about 0.1 to about 15 wt. %. In some embodiments, the third polysaccharide is present in an amount of from about 1 to about 7.5 wt %. In one or more embodiments, the third polysaccharide is selected from the group consisting of maltodextrin, starch, glucose, xantham gum, and combinations thereof. In some embodiments, the composition further comprises water. In one or more embodiments, the water is present in an amount of from about 15 to about 95 wt. %. In some embodiments, the humectant is selected from the group consisting of glycerin, propane diol, sorbitol, and combinations thereof. In one or more embodiments, the composition is in the form of a gel. In some embodiments, the composition is substantially free from a synthetic polymer.

Another aspect of the invention pertains to a composition comprising:
(a) inulin;
(b) carrageenan;
(c) maltodextrin; and
(d) a humectant.

In one or more embodiments, the hairstyling composition comprises:
(a) about 0.5 to about 3 wt % inulin;
(b) about 2 to about 6 wt % carrageenan;
(c) about 3 to about 7 wt % maltodextrin; and
(d) about 3 to about 7 wt % of a humectant.

In some embodiments, the humectant comprises glycerin. In one or more embodiments, the composition is substantially free from a synthetic polymer. In some embodiments, the hairstyling composition is in the form of a gel.

Another aspect of the invention pertains to methods of styling hair. The methods comprise applying any of the above compositions to hair.

DETAILED DESCRIPTION

Figure 1:
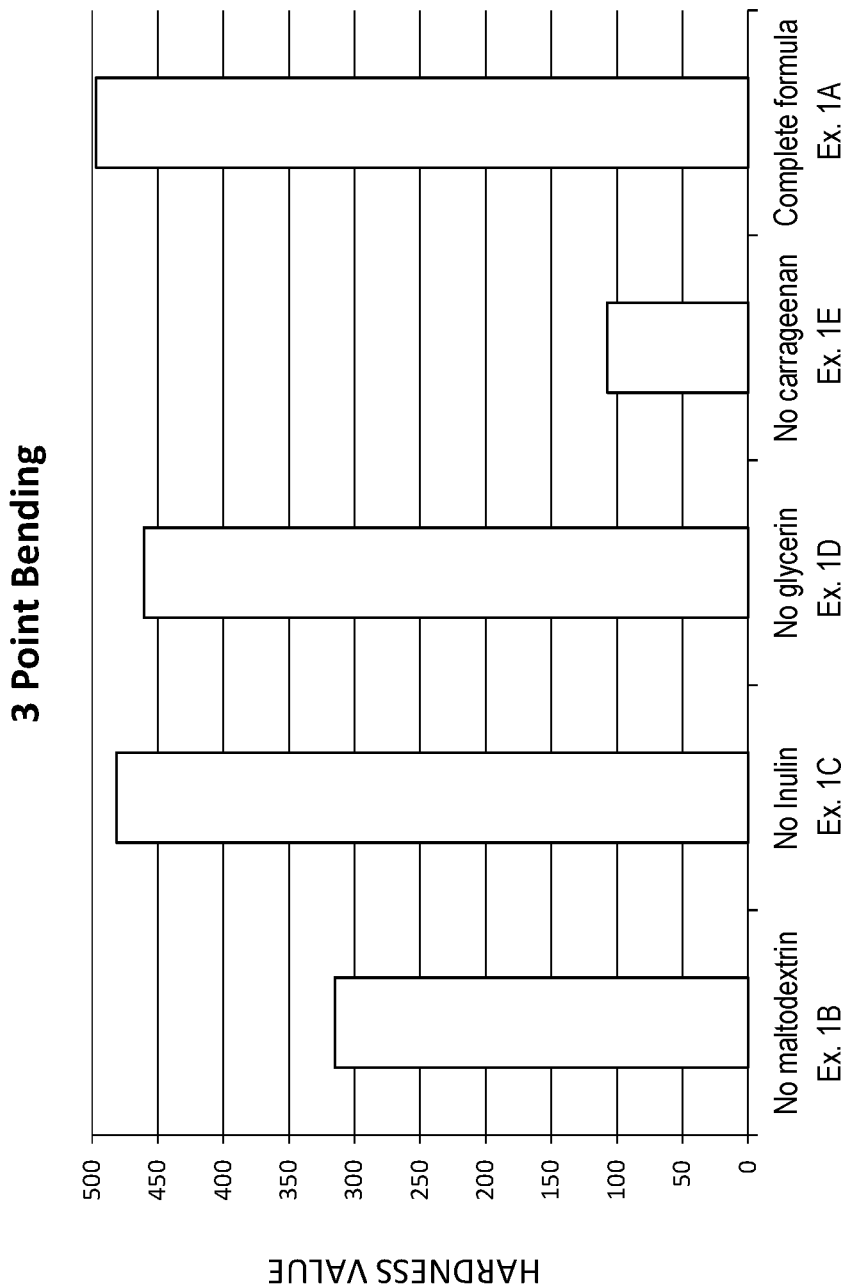
FIG. 1 is a bar graph showing hardness values for one example according to one or more embodiments of the invention, as well as four comparative examples.

The compositions of the instant disclosure are useful as leave-on hair styling for enhancing the appearance and feel of hair. The compositions include a unique combination of inulin, carrageenan a third polysaccharide and a humectant. The synergy amongst these components results in compositions that provide desirable cosmetic properties to the hair, such as holding ability, shine, styling memory and ease of distribution. The leave-on hair styling compositions typically include:
(a) a first polysaccharide comprising inulin;
(b) a second polysaccharide comprising carrageenan;
(c) a third polysaccharide; and
(d) a humectant.

It has been surprisingly discovered that said compositions can provide desirable cosmetic styling properties to hair without the use of synthetic film formers and/or silicones. Traditional hair styling products contain silicones, synthetic conditioning agents, and synthetic polymers in order to obtain a smooth look and feel. These synthetic materials however weigh down the hair, and cause the hair to feel dirty and greasy over time. Furthermore, because of the natural ingredients used in the compositions, upon application to the hair, the compositions have a clean, natural, and light-weight feel.

The hair styling compositions of the instant disclosure are unique in that they do not require synthetic polymers such as synthetic film-forming polymers. In fact, the leave-on hair styling compositions do not necessarily require any synthetic ingredients. In some cases, synthetic film-forming polymer or synthetic polymer may be included but in other cases, they may be excluded. The term "synthetic polymer" (or "synthetic film-forming polymer") means a polymer, which is purely synthetic, or not of natural origin, especially those polymers, which are made by radical polymerization of ethylenically unsaturated monomers or by polycondensation. The term "natural polymer" means a polymer of natural origin, which includes those that have been subsequently chemically or physically modified (but retains at least 50% of its molecular structure from the original natural source). In particular, the term "natural original ingredient" refers to one of the following:

1. An ingredient which remains unchanged from its natural state; or
2. An ingredient which has undergone chemical or other processing which modifies it from its natural state but which retains at least 50% of its molecular structure from the original natural source.

A naturally derived ingredient may be processed to improve its stability, efficacy and/or safety for use in leave-on hair styling products. The degree of processing varies for each ingredient, but at the end only an ingredient that retains at least 50% of its molecular structure from the original natural source is considered natural origin. In some cases, the leave-on hair styling compositions of the instant disclosure are "natural leave-on hair styling compositions." A "natural leave-on hair styling composition" is a leave-on hair styling composition comprising only "natural original ingredients," as defined above.

Non-limiting examples of synthetic film-forming polymers (which in some cases may be excluded from the instant leave-on hair styling compositions) include non-ionic hair-fixing polymers (e.g., copolymerizates of vinyl pyrrolidone and vinyl acetate, terpolymers of vinyl pyrrolidone, vinyl acetate and vinyl propionate, polyacrylamides, polyvinyl alcohols and polyethylene glycol/polypropylene glycol copolymers. Polyvinyl pyrrolidone, polyvinyl caprolactam and their copolymers with at least one further nonionic monomer, for example, polyvinylpyrrolidone/vinyl acetate copolymers) and anionic hair-fixing polymers such as synthetic homo- or copolymers with neutralizable monomer units containing acid groups, which are copolymerizable with comonomers, if necessary, which contain no acid groups. The acid groups may include —COOH, —SO3H, —OSO3H, —OPO2H, —P03H2. The acid groups can be unneutralized, or partially or completely neutralized.

Furthermore, the leave-in hair styling compositions do not require silicones (silicone and silicone containing materials). Non-limiting examples of silicones (which may optionally excluded from the instant leave-on hair styling compositions) include dimethicone, dimethiconol, amodimethicone, cyclomethicones, amino-modified silicones, and polyether-modified silicones Polysaccharides The compositions described herein contain a combination of at least three polysaccharides:

(a) a first polysaccharide comprising inulin;
(b) a second polysaccharide comprising carrageenan;
(c) a third polysaccharide.

Inulin refers to a class of polysaccharides produced by a variety of plants, and is an example of a fructan polysaccharide (also referred to as just "fructan") are polymers of fructose molecules. Inulin is commonly extracted from chicory root, and may contain (2→1) linked β-d-fructosyl residues (n=2-60), usually with an (1↔2) α-d-glucose end group. The inulin may be present in amounts ranging from about 0.1, 0.2, 0.3, 0.4, 0.5, 0.6, 0.7, 0.8, 0.9, 1, 1.1, 1.2, 1.3, 1.4, or 1.5 to about 1.5, 2, 2.5, 3, 3.5, 4, 4.5, 5, 6, 7, 8, 9 or 10 wt. % by total weight of the composition. In further embodiments, the inulin is present in an amount of from about 0.1 to about 10 wt. %, or about 0.5 to about 2.5 wt. %.

Carrageenan refers to a family of linear sulfated polysaccharides, which are commonly are extracted from red edible seaweeds. They are generally high-molecular-weight polysaccharides, and contain repeating galactose units and 3,6 anhydrogalactose (3,6-AG), both sulfated and nonsulfated. The units are joined by alternating α-1,3 and β-1,4 glycosidic linkages. The carrageenan may be present in amounts ranging from about 0.1, 0.2, 0.3, 0.4, 0.5, 0.6, 0.7, 0.8, 0.9, 1, 1.1, 1.2, 1.3, 1.4, 1.5, 2, 2.5, 3, 3.5, or 4 to about 4, 4.5, 5, 6, 7, 8, 9 or 10 wt. % by total weight of the composition. In further embodiments, the inulin is present in an amount of from about 0.1 to about 10 wt. %, or about 0.5 to about 6 wt. %.

The third polysaccharide may be of a different class from inulin and carrageenan, or may be related. In some embodiments, the third polysaccharide may comprise cellulose, carboxymethylcellulose, hydroxyethylcellulose, hydroxypropylcellulose, hydroxypropylmethylcellulose, methylcellulose, starch, starch acetate, hydroxyethyl starch, hydroxypropyl starch, guar gum, carboxymethyl guar gum, carboxymethylhydroxypropylguar gum, hydroxyethyl guar gum, hydroxypropyl guar gum, xylose or xanthan gum, cellobiose, maltodextrin, scleroglucan, chitosan, ulvan, fucoidan, alginate, pectin, heparin and hyaluronic acid, xantham gum or mixtures thereof. The third polysaccharide may also be a polysaccharide comprised of glucose subunits.

In some embodiments, the third polysaccharide may be a starch polysaccharide or a hydrolyzed starch. Non-limiting examples of hydrolyzed starch include dextrin and maltodextrin. In some embodiments, the third polysaccharide comprises maltodextrin. Maltodextrin may be produced by starch by partial hydrolysis. Maltodextrin is generally comprised of D-glucose units connected in chains of variable length, and typically composed of a mixture of chains that vary from about three to about 17 glucose units long. The glucose units are primarily linked with a α(1→4) glycosidic bonds.

The third polysaccharide (e.g., maltodextrin) may be present in amounts ranging from about 0.1, 0.2, 0.3, 0.4, 0.5, 0.6, 0.7, 0.8, 0.9, 1, 1.1, 1.2, 1.3, 1.4, 1.5, 2, 2.5, 3, 3.5, 4 or 5 to about 4, 4.5, 5, 6, 7, 7.5, 8, 9, 10, 11, 12, 13, 14 or 15 wt. % by total weight of the composition. In further embodiments, the inulin is present in an amount of from about 0.1 to about 15 wt. %, or about 1 to about 7.5 wt. %.

Fructan polysaccharides also include levan polysaccharide (also referred to as just "levan"). In some instances, the leave-on hair styling compositions include inulin polysaccharides; in some cases the leave-on hair styling compositions do not comprise levan polysaccharides, or are substantially free of levan polysaccharides.

Humectants

The compositions described herein contain at least one humectant. Humectants are hygroscopic compounds which help to retain moisture in the hair. In one or more embodiments, the humectant is selected from the group consisting of glycerin, propylene glycol (propane diol), sorbitol, butylene glycol, ethylene glycol, polyethylene glycols having from 4 to 250 repeating ethylene glycol units, ethoxydiglycol, and mixtures thereof. In further embodiments, the humectant is selected from the group consisting of glycerin, propane diol, sorbitol, and combinations thereof. In further embodiments, the humectant comprises glycerin.

The humectant may be present in amounts ranging from greater than about 0 or from about 0.1, 0.5, 1, 2, 3, 4 or 5 to about 5, 6, 7, 8, 9, 10, 15, 20 or 25 wt. %.

Other Additives

Solvents

The leave-on hair styling compositions typically include water and therefore may be referred to as "aqueous compositions." The total amount of water can vary but is typically about 15 wt. % to about 95 wt. %, based on the total weight of the leave-on hair styling composition. The total amount of water may be about 20 wt. % to about 95 wt. %, about 30 wt. % to about 95 wt. %, about 40 wt. % to about 95 wt. %, about 50 to about 95 wt. %, about 60 to about 95 wt. %, about 70 wt. % to about 95 wt. %, about 80 wt. % to about 95 wt. %, or about 85 wt. % to about 92 wt. %.

Surfactants

Cationic Surfactants

The term "cationic surfactant" means a surfactant that is positively charged when it is contained in the composition according to the disclosure. This surfactant may bear one or more positive permanent charges or may contain one or more functions that are cationizable in the composition according to the disclosure.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Anionic Surfactants

The term "anionic surfactant" means a surfactant comprising, as ionic or ionizable groups, only anionic groups. These anionic groups are chosen preferably from the groups CO2H, CO2-, SO3H, SO3-, OSO3H, OSO3-O2PO2H, O2PO2H and O2PO22-.

The anionic surfactant(s) that may be used may be alkyl sulfates, alkyl ether sulfates, alkylamido ether sulfates, alkylaryl polyether sulfates, monoglyceride sulfates, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

The salts of C6-C24 alkyl monoesters of polyglycoside-polycarboxylic acids may be chosen from C6-C24 alkyl polyglycoside-citrates, C6-C24 alkyl polyglycoside-tartrates and C6-C24 alkyl polyglycoside-sulfo succinates.

When the anionic surfactant(s) are in salt form, they may be chosen especially from alkali metal salts such as the sodium or potassium salt and preferably the sodium salt, ammonium salts, amine salts and in particular amino alcohol salts, or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used.

Mention is also made of (C6-C24)alkyl sulfates, (C6-C24)alkyl ether sulfates, which are optionally ethoxylated, comprising from 2 to 50 ethylene oxide units, and mixtures thereof, in particular in the form of alkali metal salts or alkaline-earth metal salts, ammonium salts or amino alcohol salts. In some cases, the anionic surfactant(s) are chosen from (C10-C20)alkyl ether sulfates, and in particular sodium lauryl ether sulfate containing 2.2 mol of ethylene oxide.

Amphoteric Surfactants

Amphoteric surfactants useful in the cosmetic compositions disclosed herein may be chosen from betaines, sultaines, amphoacetates, amphoproprionates, and mixtures thereof. More typically, betaines and amphoproprionates are used, and most typically betaines. Betaines which can be used in the current compositions include those having the formulas below:

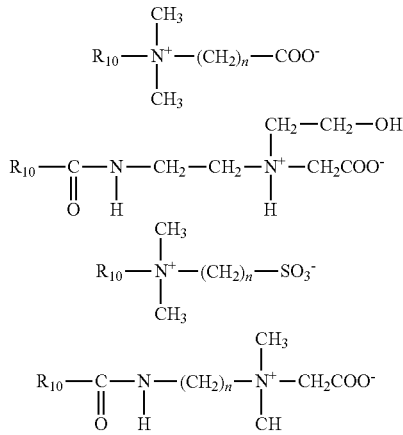

wherein

R[10] is an alkyl group having 8-18 carbon atoms; and n is an integer from 1 to 3.

Particularly useful betaines include, for example, coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coco betaine, cocoamidopropyl betaine, behenyl betaine, capryl/capramidopropyl betaine, lauryl betaine, and mixtures thereof, and more typically coco betaine.

Hydroxyl sultaines useful in the compositions of the invention include the following

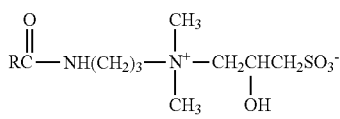

wherein

R is an alkyl group having 8-18 carbon atoms.

Useful alkylamphoacetates include those having the formula

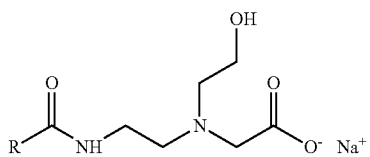

wherein

R is an alkyl group having 8-18 carbon atoms.

Useful alkyl amphodiacetates include those having the formula

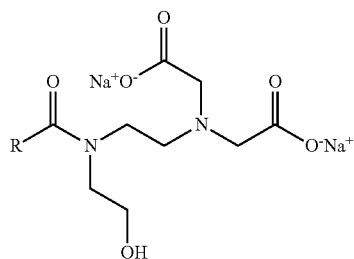

wherein

R is an alkyl group having 8-18 carbon atoms.

The amphoteric surfactants of the present disclosure may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Non-Ionic Surfactants

Nonionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol (C6-C24)alkylpolyglycosides; N—(C6-C24)alkylglucamine derivatives, amine oxides such as (C10-C14)alkylamine oxides or N—(C10-C14)acylaminopropylmorpholine oxides; and mixtures thereof.

The nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a C8-C24, preferably C12-C22, fatty acid or acids and alkoxylated derivatives thereof, preferably with a number of alkyleneoxide of from 10 to 200, and more preferably from 10 to 100; polyethylene glycol esters of a C8-C24, preferably C12-C22, fatty acid or acids and alkoxylated derivatives thereof, preferably with a number of alkyleneoxide of from 10 to 200, and more preferably from 10 to 100; sorbitol esters of a C8-C24, preferably C12-C22, fatty acid or acids and alkoxylated derivatives thereof, preferably with a number of alkyleneoxide of from 10 to 200, and more preferably from 10 to 100; sugar (sucrose, glucose, alkylglycose) esters of a C8-C24, preferably C12-C22, fatty acid or acids and alkoxylated derivatives thereof, preferably with a number of alkyleneoxide of from 10 to 200, and more preferably from 10 to 100; ethers of fatty alcohols; ethers of sugar and a C8-C24, preferably C12-C22, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can in particular be cited.

As glyceryl esters of C8-C24 alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1N by Goldschmidt (CTFA name: glyceryl stearate SE), can also be used.

Cationic Conditioning Agents

The cationic conditioning agents that may be employed in the compositions of the present disclosure can be a monoalkyl quaternary amine, such as stearyltrimonium chloride, soyatrimonium chloride or coco-ethyldimonium ethosulfate. Other suitable cationic conditioning agents include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic conditioning agents may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic conditioning agents are cationic polymers. The term "cationic polymer" means any polymer comprising at least one cationic group and/or at least one group that may be ionized into a cationic group.

Particularly useful cationic polymers in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Particularly preferred cationic polymers of the present invention include POLYMER JR-125, POLYMER JR-400, Polymer JR-30M hydroxyethyl cellulosic polymers (polyquaternium 10) available from AMERCHOL; JAGUAR C® 13-S, guar hydroxypropyltrimonium chloride, available from Rhodia; and MERQUAT® 100 and 280, a dimethyl dialkyl ammonium chloride (polyquaternium 6) available from Nalco.

The cationic polymer is generally present in an amount of from greater than 0% to about 15%, preferably from about 0.5% to about 10% by weight, and more preferably from about 1% to about 5% by weight, based on the total weight of the composition.

Cationic polymers useful herein include polyquaternium 4, polyquaternium 6, polyquaternium 7, polyquaternium 10, polyquaternium 11, polyquaternium 16, polyquaternium 22, and polyquaternium 32. Cationic polymers useful in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, and guar hydroxypropyltrimonium chloride. Preferred cationic polymers include POLYMER JR-125, POLYMER JR-400, Polymer JR-30M hydroxyethyl cellulosic polymers (polyquaternium 10) available from AMERCHOL; JAGUAR C13-S, guar hydroxypropyltrimonium chloride, available from Rhodia; and MERQUAT 100 and 280, a dimethyl dialkyl ammonium chloride (polyquaternium 6) available from Nalco.

Oils

The hair styling composition may include one or more oils, for example, silicone oils, fluoro oils, hydrocarbon-based oils, etc. The term "oil" means any fatty substance which is in liquid form at room temperature (20-25° C.) and at atmospheric pressure (760 mmHg). Often, at least one of the oils in the cosmetic composition is part of an oily phase. An "oily phase" is a phase comprising at least one oil that may include additional liposoluble and lipophilic ingredients and the fatty substances. The oily phase can be combined with an aqueous phase in an emulsion. Oil that is suitable for use herein may be volatile or non-volatile. The term "volatile oil" relates to oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa ($10^{-3}$ to 300 mmHg). The term "non-volatile oil" relates to oil which remains on the skin or the keratin fiber, at room temperature and atmospheric pressure, for at least several hours and which in particular has a vapor pressure of less than $10^{-3}$ mmHg (0.13 Pa).

The term "silicone oil" relates to oil comprising at least one silicon atom, and especially at least one Si—O group. The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil. Further, suitable oil may be a mineral hydrocarbon-based oil, a plant hydrocarbon-based oil, or a synthetic hydrocarbon-based oil.

Silicone Oils

The cosmetic compositions described herein may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Other examples of silicone oils that may be mentioned include volatile linear or cyclic silicone oils, especially those with a viscosity 8 centistokes ($8 \times 10^6$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Fluoro Oils

The cosmetic compositions described herein may comprise one or more fluoro oils. For example, the onee or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The cosmetic compositions described herein may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the compositions include a synthetic oil selected from the group consisting of hydrogenated polyisobutene and hydrogenated polydecene.

The hydrocarbon-based oil may be a non-volatile hydrocarbon-based, such as:

(i) hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, *quinoa* oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and 4 0 squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ≥10, for instance Purcellin oil (cetearyl octanoate), isopropyl myristate, isopropyl palmitate, C12-C15 alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear C14-C15 alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC® by Cognis;

(viii) fatty amides, such as isopropyl N-lauroyl sarcosinate, such as the product sold under the trade name Eldew SL 205® from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

In certain instances, the non-volatile hydrocarbon-based oils are glyceride triesters and in particular to caprylic/capric acid triglycerides, synthetic esters and in particular isononyl isononanoate, oleyl erucate, C12-C15 alkyl benzoate, 2-ethylphenyl benzoate and fatty alcohols, such as octyldodecanol.

As volatile hydrocarbon-based oils, mention is made of hydrocarbon-based oils containing from 8 to 16 carbon atoms and in particular of branched C8-C16 alkanes, such as C8-C16 isoalkanes of petroleum origin (also known as isoparaffins), such as isododecane (also known as 2,2,4,4,6-pentamethylheptane), isodecane or isohexadecane, the oils sold under the Isopar or Permethyl trade names, branched C C8-C16 esters, and isohexyl neopentanoate.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldehyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The total amount of the one or more preservatives, when present, may vary. In some cases, the total amount of the one or more preservatives is about 0.01 to about 5 wt. %, about 0.01 to about 4 wt. %, about 0.15 to about 1 wt. %, or about 1 to about 3 wt. %, based on the total weight of the composition.

Suitable components, such as those listed in the instant disclosure (including those listed above), may be included or excluded from the hair styling compositions depending on the specific combination of other components, the form of the compositions, and/or the use of the formulation (e.g., hair spray, cream, paste, conditioner, etc.).

Methods

The leave-on hair styling compositions may be used in various methods for treating hair, for example, human hair, including human hair one an individual's head. For example, the compositions are useful for: (i) providing hold to hair; (ii) providing style memory to hair; (iii) providing style/shape control; (iv) providing discilpline; (v) and being easy to distribute throughout the hair; wherein the methods typically comprise applying a hair styling composition disclosed herein to the hair. The methods may include applying the leave-on hair styling composition to the hair, subsequently styling the hair while allowing the leave-on hair styling composition to remain on the hair, for example, for one or more hours, or one or more days before being removed by a subsequent washing. The leave-on hair styling composition may be applied to wet, damp, or already dry hair. Once applied, the hair may be manipulated (e.g., with a comb, brush or hands) to achieve the desired shape.

Exemplary Embodiments

In one or more embodiments, the composition is a hair-styling composition, and comprises:
(a) inulin;
(b) carrageenan;
(c) maltodextrin; and
(d) a humectant.

In further embodiments, the composition comprises:
(a) about 0.5 to about 3 wt % inulin;
(b) about 2 to about 6 wt % carrageenan;
(c) about 3 to about 7 wt % maltodextrin; and
(d) about 3 to about 7 wt % of a humectant.

As described above, the humectant may comprise glycerin. The compositions may also be substantially free of a synthetic polymer. In some embodiments, the composition is in the form of a gel.

Physical Form

The leave-on hair styling compositions described herein may be in any suitable physical form. Suitable forms include, but are not limited to low to moderate viscosity liquids, lotions, milks, mousses, sprays, gels, creams, pastes, clays, bars, conditioners, and the like. For instance, spray formulations may be dispensed from containers that include aerosol dispensers or pump spray dispensers. Such dispensers are known in the art and are commercially available from a variety of manufacturers. When the spray formulation is dispensed from a pressurized aerosol container, a propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed. Furthermore, the leave-on hair styling compositions may be in the form of an emulsion (e.g., water-in-oil or oil-in-water emulsion). In some cases, the leave-in hair styling composition is in the form of a paste, which may be a semi-solid product that can be applied throughout the hair using one's fingers.

In preferred embodiments, the composition is in the form of a gel.

As suggested by the term "leave-on hair styling compositions," these compositions are formulated so that they can remain on the hair for extended periods of time, i.e., the compositions are applied to the hair, for example, during styling of the hair and allowed to remain for one or more hours, or one or more days before being removed, for example, by washing. In other words, the leave-on hair styling compositions are applied to the hair and allowed to remain on the hair without immediate rinsing or removal. The leave-on hair styling compositions may be applied to the hair, for example, after shampooing, before or during the styling process. The hair may be wet, damp, or already dry when the hair styling composition is applied to the hair. In some cases, the leave-on hair styling composition may be applied to wet or damp hair after which the hair is blow dried and styled. In other cases, the hair may be previously dried and the leave-on hair styling composition is applied to dry hair, in order to treat, shape, or style the hair.

The leave-on hair styling compositions may be packaged in a variety of different containers, such as, for example, a ready-to-use container. Non-limiting examples of useful packaging include tubes, jars, caps, unit dose packages, and bottles, including squeezable tubes and bottles. The packaging may be configured so that it can be attached to a wall, such as a wall in a bathroom, including walls of a shower or tub. For example, the packaging can be a container that is configured to attach to a wall, such that when pressure is applied to the container, the composition contained therein is expelled from one or more openings in the bottom of the container.

Implementation of the present disclosure is provided by way of the following examples. The examples serve to illustrate the technology without being limiting in nature.

EXAMPLES

Example 1

Three Point Bending

Five compositions (Examples 1A-1E) were prepared having the ingredients shown below in Table 1. Example 1A is inventive, while Examples 1B-1E were comparative, each missing one claimed ingredient and the balance made up with water.

TABLE 1

|     |                                                     | INCI US           | Ex. 1A (Inv.) | Ex. 1B (Comp.) | Ex. 1C (Comp.) | Ex. 1D (Comp.) | Ex. 1E (Comp.) |
|-----|-----------------------------------------------------|-------------------|---------------|----------------|----------------|----------------|----------------|
| (a) | Polysaccharide                                      | Inulin            | 1.455         | 1.455          | —              | 1.455          | 1.455          |
| (b) | Polysaccharide                                      | Carrageenan       | 4             | 4              | 4              | 4              | —              |
| (c) | Polysaccharide                                      | Maltodextrin      | 4.917         | —              | 4.917          | 4.917          | 4.917          |
| (d) | Humectant                                           | Glycerin          | 5             | 5              | 5              | —              | 5              |
|     | Solvent                                             | Water             | 83.045        | 88.145         | 84.5           | 88.045         | 87.045         |
|     | Solvent                                             | Caprylyl Glycol   | 0.3           | 0.3            | 0.3            | 0.3            | 0.3            |
|     | Fragrance, Preservative, Vegetable Extracts         | Miscellaneous     | 1.283         | 1.1            | 1.283          | 1.283          | 1.283          |
|     |                                                     | Total             | 100           | 100            | 100            | 100            | 100            |

The individual influence of each of the main components of the composition of was investigated by evaluating the hardness of a film formed from the composition.

Virgin hair swatches were washed with a cleansing shampoo and rinsed with water. 0.5 g of formula were applied to each swatch, and three swatches were prepared for each of Examples 1A-1E. The swatches were allowed to dry overnight. The swatches were then placed onto a Brookfield Texture Analyzer (Model CT3 4500) and analyzed for hardness value. The "hardness" is the breaking strength or breaking stress of the sample. A force (load) is applied to the sample breaking the film on the hair which is turn gives a hardness value. The higher the hardness value, the more force required to break the film on the hair, correlating to a stronger hold of the formula. The results are shown in FIG. 1. As seen in FIG. 1, inventive Ex. 1A exhibited the highest hardness value compared to any of the comparative formulas, thus demonstrating a synergistic effect in the association of ingredients.

Example 2

Hair Styling Benefits

The individual influence on the hair styling benefits of each of the main components of the inventive composition was investigated. The ingredients and hair styling benefits investigated are shown below in Table 2.

TABLE 2

| | Hair Styling Benefit | | | | | | | |
|---|---|---|---|---|---|---|---|---|
| Raw Material | Hold | Stiffness | Style Memory | Style/Shape Control | Shine | Discipline | Rheology | Ease of Distribution |
| Carrageenan | ✓ | | ✓ | ✓ | | | ✓ | |
| Maltodextrin | ✓ | ✓ | | | | | | |
| Inulin | ✓ | | | | ✓ | ✓ | | |
| Glycerin | ✓ | | | | ✓ | | | ✓ |
| Carrageenan Maltodextrin | ✓ | ✓ | ✓ | ✓ | | | ✓ | |
| Carrageenan Inulin | ✓ | | ✓ | ✓ | ✓ | ✓ | ✓ | |
| Maltodextrin Inulin | ✓ | ✓ | | | ✓ | ✓ | | |
| Inulin Glycerin | ✓ | | | | ✓ | ✓ | | ✓ |
| Carrageenan Maltodextrin Inulin Glycerin | ✓ | ✓ | ✓ | ✓ | ✓ | ✓ | ✓ | ✓ |

"✓" indicates that the benefit reached an acceptable level.

Each of the samples contained the ingredient indicated, with the balance made up with water. The various styling benefits were evaluated qualitatively.

As can be seen in Table 2, it is only when all of the claimed ingredients are present that all of the hair styling benefits are exhibited.

Example 3

Three Point Bending

Three samples were prepared with the ingredients listed according to Table 3 below. Example 3A is inventive, and has the same formula as Example 1A above. Examples 3B and 3C are comparative, as they do not contain carrageenan, and instead contain either hydroxyethyl cellulose or acacia Senegal gum (two alternative natural polysaccharides) in the same amount as carrageenan.

TABLE 3

|     |                                             | INCI US              | Ex. 3A (Inv.) | Ex. 3B (Comp.) | Ex. 3C (Comp.) |
| --- | ------------------------------------------- | -------------------- | ------------- | -------------- | -------------- |
| (a) | Polysaccharide                              | Inulin               | 1.455         | 1.455          | 1.455          |
| (b) | Polysaccharide                              | Carrageenan          | 4             | —              | —              |
|     | Polysaccharide                              | Hydroxyethyl-Cellulose | —           | 4              | —              |
|     | Polysaccharide                              | Acacia Senegal Gum   | —             | —              | 4              |
| (c) | Polysaccharide                              | Maltodextrin         | 4.917         | 4.917          | 4.917          |
| (d) | Humectant                                   | Glycerin             | 5             | 5              | 5              |
|     | Solvent                                     | Water                | 83.045        | 83.045         | 83.045         |
|     | Solvent                                     | Caprylyl Glycol      | 0.3           | 0.3            | 0.3            |
|     | Fragrance, Preservative, Vegetable Extracts | Miscellaneous        | 1.283         | 1.283          | 1.283          |
|     |                                             | TOTAL                | 100           | 100            | 100            |

Figure 2:
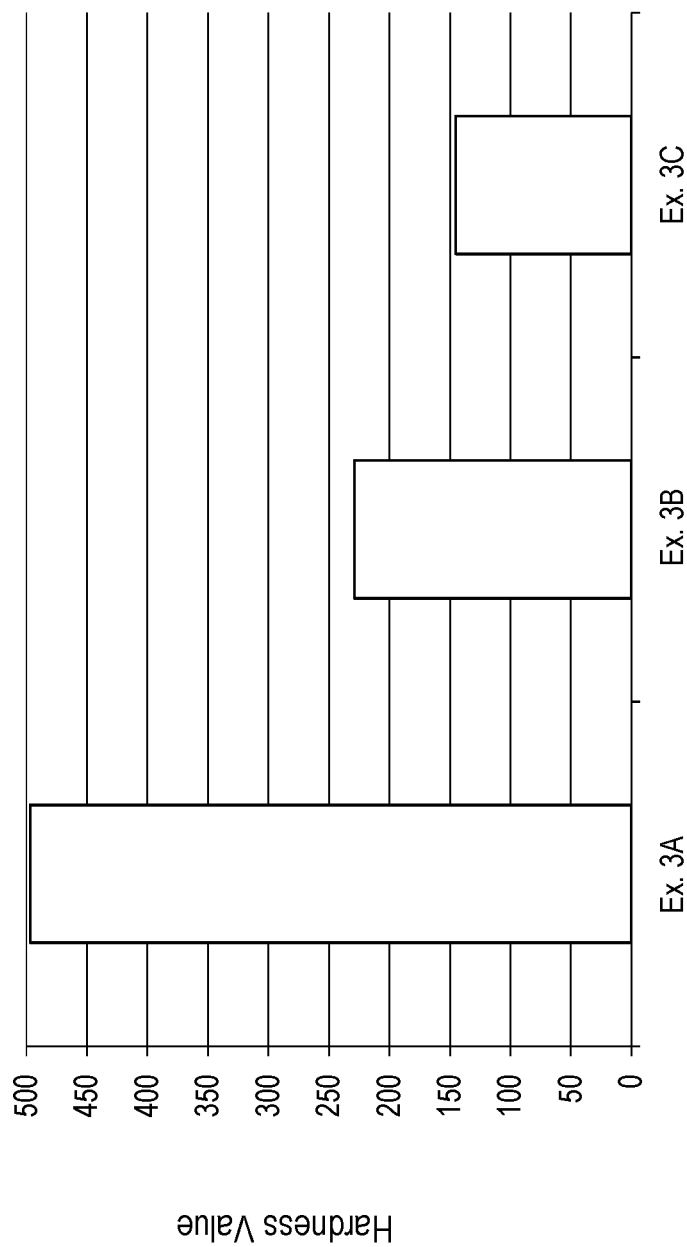
FIG. 2 is a bar graph showing hardness values for one example according to one or more embodiments of the invention, as well as two comparative examples.

Nine virgin hair swatches were washed with a cleansing shampoo and rinsed with water. 0.5 g of formula were applied to each swatch, and three swatches were prepared for each of Examples 3A-3C. The swatches were allowed to dry overnight. The swatches were then placed onto a Brookfield Texture Analyzer (Model CT3 4500) and analyzed for hardness value. The average hardness value (in grams of force) for each formula is shown in FIG. 2. As seen in FIG. 2, inventive Example 3A is significantly harder than either comparative Examples 3B or 3C. This demonstrates carrageenan as an important polysaccharide, and it cannot be merely substituted with other polysaccharides.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present disclosure, unless otherwise indicated.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 2% by weight of a specific material added to a composition, based on the total weight of the compositions. The components described for optional inclusion in the compositions of the disclosure may be free of the component(s) or may be "substantially free" or "essentially free" of the component(s). Nonetheless, the compositions may include less than about 1 wt. %, less than about 0.5 wt. %, less than about 0.1 wt. %, or none of the specified material.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A composition comprising:
   (a) about 0.1 to about 10 wt. % of inulin;
   (b) about 0.01 to about 10 wt. % of carrageenan;
   (c) about 0.1 to about 15 wt. % of a polysaccharide other than inulin and carrageenan; and
   (d) a humectant; and
   (e) about 15 to about 95 wt.b% of water.

2. The composition of claim 1, wherein the composition does not comprise a levan polysaccharide.

3. The composition of claim 1, wherein the inulin is present in an amount of from about 0.5 to about 2.5 wt. %.

4. The composition of claim 1, wherein the carrageenan is present in an amount of from about 0.5 to about 6 wt. % by weight of the total composition.

5. The composition of claim 1, wherein the polysaccharide other than inulin and carrageenan is present in an amount of from about 1 to about 7.5 wt %.

6. The composition of claim 1, wherein the polysaccharide other than inulin and carrageenan is selected from the group consisting of maltodextrin, starch, glucose, xantham gum, and combinations thereof.

7. The composition of claim 1, wherein the humectant is selected from the group consisting of glycerin, propane diol, sorbitol, and combinations thereof.

8. The composition of claim 1, wherein the composition is in the form of a gel.

9. The composition of claim 1, wherein the composition is substantially free from a synthetic polymer.

10. A hairstyling composition comprising:
(a) about 0.1 to about 10 wt. % of inulin;
(b) about 0.01 to about 10 wt. % of carrageenan;
(c) about 0.1 to about 15 wt. % of maltodextrin; and
(d) a humectant; and
(e) about 15 to about 95 wt. % of water.

11. The hairstyling composition of claim 10, wherein the composition comprises:
(a) about 0.5 to about 3 wt % inulin;
(b) about 2 to about 6 wt % carrageenan;
(c) about 3 to about 7 wt % maltodextrin; and
(d) about 3 to about 7 wt% of a humectant; and
(e) about 15 to about 95 wt. % of water.

12. The hairstyling composition of claim 11, wherein the humectant comprises glycerin.

13. The hairstyling composition of claim 11, wherein the composition is substantially free from a synthetic polymer.

14. The hairstyling composition of claim 11, wherein the hairstyling composition is in the form of a gel.

15. The hair styling composition of claim 1 that is free of acylsarcosinates and alkyl sulfoacetates.

16. The hair styling composition of claim 10 that is free of acylsarcosinates and alkyl sulfoacetates.

17. The hair styling composition of claim 11 that is free of acylsarcosinates and alkyl sulfoacetates.

18. The hair styling composition of claim 1 that is free of anionic surfactants.

19. The hair styling composition of claim 10 that is free of anionic surfactants.

* * * * *

UNITED STATES PATENT AND TRADEMARK OFFICE
CERTIFICATE OF CORRECTION

Page 1 of 1

PATENT NO. : 10,729,637 B2
APPLICATION NO. : 15/907780
DATED : August 4, 2020
INVENTOR(S) : Sana Ghani, Aziza Khader Suleiman and Vanessa Decarlo It is certified that error appears in the above-identified patent and that said Letters Patent is hereby corrected as shown below:

On the Title Page

Item (72) add:
- Anand Ramchandra MAHADESHWAR, Springfield, NJ (US) -

Signed and Sealed this
Twenty-second Day of February, 2022

Drew Hirshfeld
*Performing the Functions and Duties of the
Under Secretary of Commerce for Intellectual Property and
Director of the United States Patent and Trademark Office*